United States Patent [19]

Hobbs

[11] Patent Number: 5,068,237

[45] Date of Patent: Nov. 26, 1991

[54] SUBSTITUTED FURANS AND DERIVATIVES THEREOF ACTING AT MUSCARINIC RECEPTORS

[75] Inventor: Sheila H. Hobbs, Dexter, Mich.

[73] Assignee: Warner-Lambert Company, Morris Plains, N.J.

[21] Appl. No.: 526,406

[22] Filed: May 21, 1990

[51] Int. Cl.$^5$ .................... A61K 31/415; C07D 405/06
[52] U.S. Cl. ..................................... 514/365; 514/374; 514/397; 514/406; 514/422; 514/444; 548/203; 548/235; 548/336; 548/374; 548/517; 549/60
[58] Field of Search .............. 548/336, 203, 235, 374, 548/517; 549/60; 514/365, 374, 397, 406, 422, 444

[56] References Cited

U.S. PATENT DOCUMENTS 4,061,722 12/1977 Rodor ................................ 514/397
4,174,451 11/1979 Granados et al. ................. 546/283

FOREIGN PATENT DOCUMENTS 2408602 6/1979 France .
1-242571 9/1989 Japan .
467325 2/1978 Spain .

OTHER PUBLICATIONS

Danheiser et al., J. Am. Chem. Soc. (111), pp. 4407-4413, (1989).

*Primary Examiner*—Bernard Dentz
*Attorney, Agent, or Firm*—Francis J. Tinney

[57] ABSTRACT

Substituted furans and derivatives thereof are described, as well as methods for the preparation and pharmaceutical compositions of same, which are useful as centrally acting muscarinic agents and are useful as analgesic agents for the treatment of pain, as sleep aids and as agents for treating the symptoms of senile dementia, Alzheimer's disease, Huntington's chorea. tardive, dyskinesia, hyperkinesia, mania, or similar conditions of cerebral insufficiency characterized by decreased cerebral acetylcholine production or release.

6 Claims, No Drawings

SUBSTITUTED FURANS AND DERIVATIVES THEREOF ACTING AT MUSCARINIC RECEPTORS

BACKGROUND OF THE INVENTION

The present invention relates to novel substituted furans and derivatives thereof useful as pharmaceutical agents, to methods for their production, to pharmaceutical compositions which include these compounds and a pharmaceutically acceptable carrier, and to pharmaceutical methods of treatment. More particularly, the novel compounds of the present invention act at muscarinic receptors and may be useful in treating the symptoms of cognitive decline in an elderly patient.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over 60 years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia, for example, the level of the enzyme choline acetyltransferase (CAT) can be reduced as much as ninety percent (see Davies, P., et al., *The Lancet*, 2, page 1403 (1976); Perry, E. K., et al., *Journal of Neurological Sciences*, 34, pages 247-265 (1977); and White, P., et al., *The Lancet*, 1, pages 668-670 (1977)).

Since CAT catalyzes the synthesis of acetylcholine from its precursors choline and acetyl coenzyme A, the loss of CAT reflects the loss of cholinergic or acetylcholine-releasing nerve endings in the hippocampus and cerebral cortex. There is abundant evidence that cholinergic terminals in the hippocampus are critically important for memory formation.

The cholinergic hypothesis suggests that drugs which restore acetylcholine levels or cholinergic function (i.e., cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction (Peterson, C. and Gibson, G. E., *Neurobiology of Aging*, 4, pages 25-30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine (see Davis, H. P., et al., *Experimental Aging Reserach*, 9, pages 211-214 (1983)).

It has been known for some time that the natural alkaloid, muscarine, has the ability to act relatively selectively at autonomic effector cells to produce qualitatively the same effect as acetylcholine. Two other agents, pilocarpine and oxotremorine, have the same principal sites of action as muscarine and acetylcholine and are thus classified as having "muscarinic" action.

It is well known that the cholinergic hypothesis suggests that cholinomimetics, including muscarinic agents, may have potential in treating senile cognitive decline (SCD). However, the multiple development issues associated with cholinomimetics, including, for example, poor bioavailability, short duration of action, and especially parasympathetic side effects, have diminished hopes of adequate therapy with this class of agents.

2-Furyl-(3,4-dimethyl-2-pyridyl)-carbinol is disclosed as an analgesic in U.S. Pat. No. 4,174,451.

2-(3-Methyl-2-furyl)-1,3,4-trimethyl-1,2,5,6-tetrahydropyridine and 2-(3-furylmethyl)-1,3,4-trimethyl-1,2,5,6-tetrahydropyridine are disclosed as analgesics in ES-467325.

Piperidine derivatives of Formula

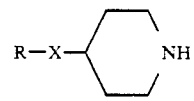

wherein X is $CH_2$, CHOH or CO and R is furyl or tetrahydrofuryl are disclosed as intermediates for pharmaceutically active quinazoline derivatives in FR-2408602.

However, none of the compounds disclosed in the aforementioned references suggest the combination of structural variations of the compounds of the present invention described hereinafter. Furthermore, the aforementioned compounds are not disclosed for treating the symptoms of cognitive decline in an elderly patient.

The substituted furans and derivatives of the present invention which are related to pilocarpine may have affinity for the muscarinic receptor and thus may be useful in treating the symptoms of cognitive decline in an elderly patient.

SUMMARY OF THE INVENTION

Accordingly, the present invention is a compound of Formula I

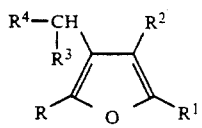

wherein R, R[1], and R[2] are each independently hydrogen, alkyl of from one to ten carbon atoms, alkynyl of from two to ten carbon atoms or aryl; R[3] is hydrogen, hydroxy, or alkoxy of from one to ten carbon atoms; and R[4] is selected from the group consisting of

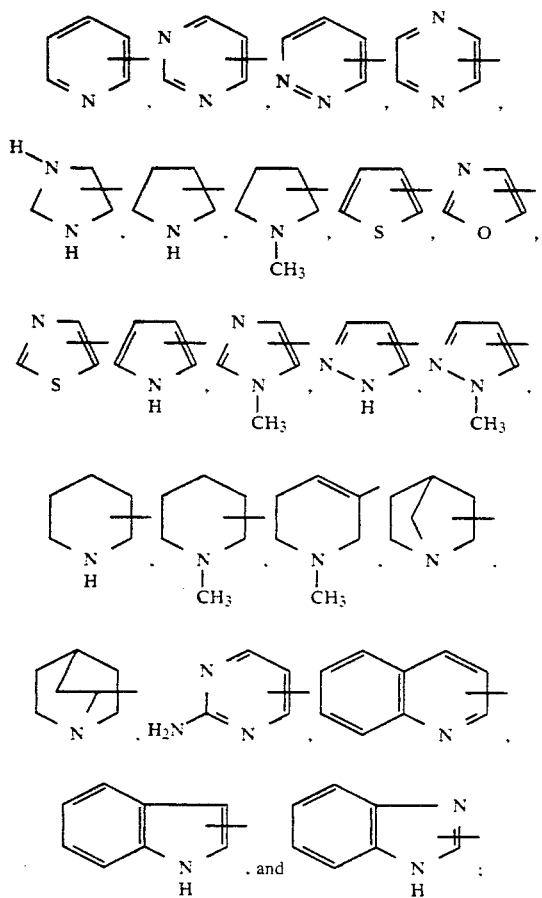

or a pharmaceutically acceptable acid addition salt thereof; with the exclusion of the compounds wherein R, R[1] and R[2] are hydrogen and R[3] is hydrogen or hydroxy and R[4] is

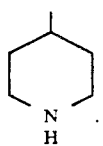

As centrally acting muscarinic agents, the compounds of Formula I are useful as analgesic agents for the treatment of pain in mammals including man, as sleep aids, and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to ten carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, and the like.

The term "alkynyl" means a straight or branched triple bonded unsaturated hydrocarbon radical having from two to ten carbon atoms and includes, for example, ethynyl, 2-propynyl, 1-butynyl, 2-butynyl, 3-butynyl, 1-pentynyl, 3-pentynyl, 1-hexynyl, 2-hexynyl, 3-hexynyl, 3-heptynyl, 1-octynyl, 2-octynyl, 1-nonynyl, 2-nonynyl, 3-nonynyl, 4-nonynyl, 1-decynyl, 2-decynyl, and the like.

The term "alkoxy" means alkyl—O— of from one to ten carbon atoms as defined above for "alkyl."

The term "thioalkoxy means alkyl—S— of from one to ten carbon atoms as defined above for alkyl".

The term "aryl" means an aromatic radical which is a phenyl group or phenyl group substituted by one to four substituents selected from alkyl, alkoxy, thioalkoxy, halogen or trifluoromethyl such as, for example, benzyl, phenethyl, and the like.

The term "alkali metal" means a metal in Group IA of the periodic table and includes, for example, lithium, sodium, potassium, and the like.

"Halogen" is fluorine, chlorine, bromine, or iodine.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S.M., et al., "Pharmaceutical Salts," *Journal of Pharmaceutical Science*, Vol. 66, pages 1-19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula I is one wherein $R^4$ is

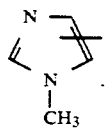

A more preferred compound of Formula I is one wherein $R^4$ is

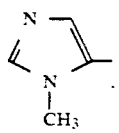

Particularly valuable are:

α-(5-Ethyl-3-furanyl)-1-methyl-1H-imidazole-2-methanol;

α-(2-Ethyl-3-furanyl)-1-methyl-1H-imidazole-2-methanol;

α-(4-Ethyl-3-furanyl)-1-methyl-1H-imidazole-2-methanol;

α-(2-Ethyl-5-methyl-3-furanyl)-1-methyl-1H-imidazole-2-methanol;

α-(4-Ethyl-5-methyl-3-furanyl)-1-methyl-1H-imidazole-2-methanol;

5-[(5-Ethyl-3-furanyl)methyl]-1-methyl-1H-imidazole;

5-[(2-Ethyl-3-furanyl)methyl]-1-methyl-1H-imidazole;

5-[(4-Ethyl-3-furanyl)methyl]-1-methyl-1H-imidazole;

5-[(2-Ethyl-5-methyl-3-furanyl)methyl]-1-methyl-1H-imidazole; and

5-[(4-Ethyl-5-methyl-3-furanyl)methyl]-1-methyl-1H-imidazole; or a pharmaceutically acceptable acid addition salt thereof.

The compounds of Formula I are valuable centrally acting muscarinic agents. The biological activity of compounds of the present invention can be evaluated using a number of tests. The activity of compounds of the present invention as central muscarinic binding site agonists and antagonists can be measured. Thus, in the Receptor [³H]Quinuclidinyl Benzilate Binding Assay (RQNB), described more fully by Watson, M., et al., *Journal of Pharmacology and Experimental Therapeutics,* 237, pages 411 to 418 (1986), rat cerebral cortex tissue is treated with radiolabeled quinuclidinyl benzilate, a known muscarinic binding site antagonist. The concentration of test compound required to inhibit 50% of the binding of this muscarinic antagonist is then determined. This procedure allows a determination of the affinity of the test compound for the central muscarinic antagonist site. Similarly, in the Receptor [³H]Cis-methyldioxalane Assay (RCMD), described more fully by Vickroy, T. W., et al., *Journal of Pharmacology and Experimental Therapeutics,* 229, pages 747 to 755 (1984), rat cerebral cortex tissue is treated with radiolabeled cis-methyldioxalane, a known muscarinic binding site agonist. The concentration of test compound required to inhibit 50% of the binding of this muscarinic agonist is then determined. This procedure allows a determination of the affinity of the test compound for the central muscarinic agonist site.

In the Muscarinic Induced Inositol Phosphate Accumulation Assay (MIPA) human SK-N-SH cells bearing muscarinic binding sites are incubated with the test compound. The production of inositol phosphates is then measured. Stimulation of inositol phosphate turnover reflects the degree of muscarinic agonist activity of the test compound. The concentration of test compound required to produce a response 50% of the maximum is then determined.

A compound of Formula Ia

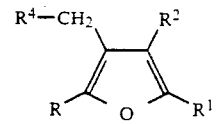

wherein R, $R^1$, and $R^2$ are each independently hydrogen, alkyl of from one to ten carbon atoms, alkynyl of from two to ten carbon atoms or aryl; and $R^4$ is selected from the group consisting of

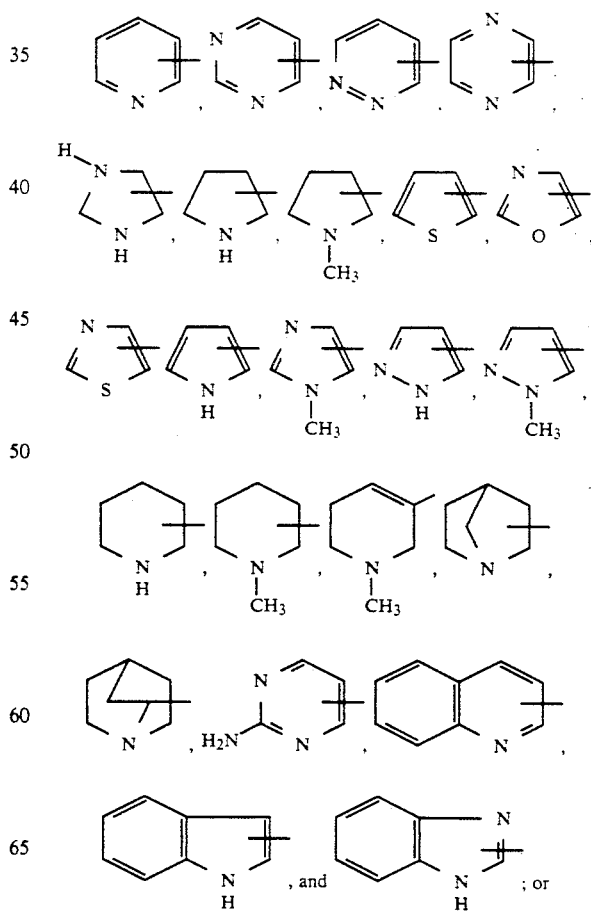

a pharmaceutically acceptable acid addition salt thereof; with the exclusion of the compound wherein R, $R^1$ and $R^2$ are hydrogen and $R^4$ is

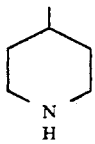

may be prepared by reacting a compound of Formula II

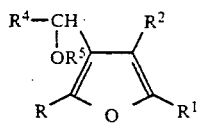  II wherein $R^5$ is

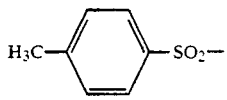

and R, $R^1$, $R^2$, and $R^4$ are as defined above with an organometallic hydride such as, for example, lithium aluminum hydride to give a compound of Formula Ia.

A compound of Formula Ib

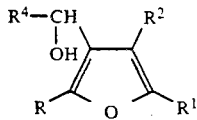  Ib wherein R, $R^1$, $R^2$, and $R^4$ are as defined above may be prepared by reacting a compound of Formula III

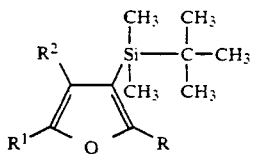  III wherein R, $R^1$, and $R^2$ are as defined above with a compound of Formula IV

R⁴—CHO    IV wherein $R^4$ is as defined above in the presence of tetrabutylammonium fluoride to give a compound of Formula Ib.

A compound of Formula Ic

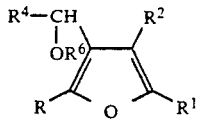  Ic wherein $R^6$ is alkyl of from one to ten carbon atoms and R, $R^1$, $R^2$, and $R^4$ are as defined above may be prepared by reacting a compound of Formula Ib with a compound of Formula V $R^6X$    V wherein X is halogen and $R^6$ is as defined above in the presence of a base such as, for example, an alkali metal hydroxide, alkali metal, and the like to give a compound of Formula Ic.

A compound of Formula II may be prepared by reacting a compound of Formula Ib with para-toluenesulfonyl chloride.

A compound of Formula III is prepared by the methodology disclosed by Danheiser, R. L., et al., *Journal of the American Chemical Society* 111, pages 4407–4413 (1989).

A compound of Formula IV is either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.7 to 7000 mg depending upon the particular application and the potency of the active component. The composition can, if desired, also contain other compatible therapeutic agents.

In therapeutic use as centrally active muscarinic agents the compounds utilized in the pharmaceutical method of this invention are administered at the initial dosage of about 0.01 to about 100 mg per kilogram daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

α-(2-Ethyl-5-methyl-3-furanyl)-1-methyl-1H-imidazole-2-methanol

Step A

Preparation of
1-(tertiary-Butyldimethylsilyl)-1-ethylallene

A 500-mL, three-necked, round-bottomed flask equipped with a low-temperature thermometer, a rubber septum, and 250-mL pressure-equalizing addition funnel is charged with 3-(tert-butyldimethylsilyl)-2-propyn-1-ol (Danheiser, R. L., et al., *Journal of the American Chemical Society*, Volume 111, pages 4407–4413 (1989)) (45.3 g, 266 mmol) and 270 mL of tetrahydrofuran and then cooled to 0° C. while methylmagnesium chloride (2.8M in tetrahydrofuran, 96 mL, 269 mmol) is added at a rate such that the internal temperature does not rise above 10° C. Approximately 1.25 hours is required for the addition, after which time the gray solution is stirred for another 30 minutes at 0° C. and then cooled below −70° C. with a dry ice-acetone bath. Methanesulfonyl chloride (30.8 g, 269 mmol) is added via a syringe over 20 minutes, and the reaction mixture is allowed to warm to room temperature over the course of 2.5 hours.

A 2-L, three-necked, round-bottomed flask equipped with a nitrogen inlet adapter and two glass stoppers is charged with copper(I) bromide (40.0 g, 279 mmol) and lithium bromide (24.2 g, 279 mmol). The reaction vessel is evacuated, and the contents are heated briefly several times over the course of 30 minutes. The vacuum is then replaced by nitrogen and the apparatus is rapidly equipped with a mechanical stirrer and two rubber septa. Tetrahydrofuran (350 mL) is added, and the resulting green solution containing a small amount of undissolved solid is cooled with an ice bath while ethylmagnesium chloride (2M in tetrahydrofuran, 135 mL, 269 mmol) is added rapidly via a syringe over 3 minutes. After 20 minutes of stirring at 0° C., the viscous yellow-green suspension is cooled below −70° C. with a dry ice-acetone bath. The solution of the mesylate derivative of 3-(tert-butyldimethylsilyl)-2-propyn-1-ol prepared above is cooled below −70° C. and transferred dropwise via a cannula over 70 minutes to the rapidly stirred suspension of the cuprate reagent. The cold bath is then removed, and the green reaction mixture is allowed to warm to room temperature over 2.5 hours. The blue-gray mixture is then poured into a 2-L Erlenmeyer flask containing a magnetically stirred mixture of 400 mL of pentane, 200 mL of water, and 400 mL of saturated ammonium chloride solution. The organic phase is separated and washed successively with two 200 mL portions of saturated ammonium chloride solution, ten 500 mL portions of water, and 100 mL of saturated sodium chloride solution. The organic phase is dried over sodium sulfate, filtered, and then concentrated by atmospheric distillation through a 4-cm Vigreaux column. The residual liquid is next carefully distilled through a 4-cm Vigreux column to provide the title compound.

Step B

Preparation of
3-(tertiary)-Butyldimethylsilyl)-2-ethyl-5-methylfuran

A 50-mL, one-necked, round-bottomed flask equipped with a three-way argon inlet adapter fitted with a rubber septum is charged with aluminum chloride (0.836 g, 6.27 mmol) and 12 mL of dichloromethane and then cooled to −20° C. while acetyl chloride (0.49 g, 6.27 mmol) is added rapidly via a syringe over the course of 1 minute. After 5 minutes, a solution of 1-(tertiary-butyldimethylsilyl)-1-ethylallene (95% purity, 1.10 g, 6.27 mmol) in 13 mL of dichloromethane is added dropwise via a syringe over the course of 1 minute. The resulting reaction mixture is stirred at −20° C. for 1 hour and then quenched by the addition of triethylamine (0.950 g, 9.39 mmol) in 25 mL of pentane. The resulting solution is stirred at room temperature for 10 minutes, diluted with an additional 25 mL of pentane, and then washed with two 50 mL portions of 10% hydrochloric acid solution, 50 mL of 3% sodium hydroxide solution, 50 mL of water, and 50 mL of saturated sodium chloride solution. The organic phase is dried over potassium carbonate, filtered, and concentrated to afford after column chromatography on silica gel the title compound.

Step C

Preparation of α-(b 2-Ethyl-5-methyl-3-furanyl)-1-methyl-1H-imidazole-2-methanol A mixture of 3-(tertiary-butyldimethylsilyl)-2-ethyl-5-methylfuran (0.21 g, 1 mmol) and N-methyl-5-imidazolecarboxaldehyde (0.17 g, 1.5 mmol) in tetrahydrofuran (3 mL) is added to tetrabutylammonium fluoride (0.1 mL, 1M in tetrahydrofuran). The resulting solution is stirred at 25° C. for 24 hours and then treated with 2N hydrochloric acid (5 mL) and extracted with dichloromethane. Removal of the solvent after drying with magnesium sulfate, followed by chromatography on silica affords the title compound.

EXAMPLE 2

5-[(2-Ethyl-5-methyl-3-furanyl)methyl]-1-methyl-1H-imidazole

Step A

Preparation of (2-Ethyl-5-methyl-3-furanyl)-(3-methyl-1H-imidazol-4-yl)methyl 4-methyl benzenesulfonate To a solution of 18.5 g (0.084 mol) of α-(2-ethyl-5-methyl-3-furanyl)-1-methyl-1H-imidazole-2-methanol (Example 1) in 25 mL of dry pyridine, cooled in an ice bath, is added a solution of 17.5 g (0.092 mole) of para-toluenesulfonyl chloride in 15 mL of pyridine at such a rate that the temperature does not rise above 10°. The reaction mixture is allowed to stand at 0° for 4 hours and then poured into 900 mL of ice-water with rapid stirring. Basification with concentrated aqueous ammonia causes a precipitate to form from which the supernatant liquid is decanted. An additional 900 mL of water is added. The precipitate is filtered and slurried two more times with 400-mL portions of water, after which it is dried to constant weight in a vacuum desiccator. The crude title compound is crystallized from toluene-hexane.

Step B

Preparation of 5-[(2-Ethyl-5-methyl-3-furanyl)methyl]-1-methyl-1H-imidazole Twenty-five milliliters of a 2.4M solution of lithium aluminum hydride in tetrahydrofuran is added to a solution of 20.6 g (0.055 mole) of (2-ethyl-5-methyl-3-furanyl)(3-methyl-1H-imidazol-4-yl)methyl 4-methyl benzenesulfonate in 100 mL of tetrahydrofuran. After the initial mild exothermic reaction (controlled by cooling in a water bath) subsides, the mixture is heated under reflux with stirring in a nitrogen atmosphere for 3 hours. To the reaction mixture, cooled in an ice bath, is then added 100 mL of diethyl ether followed by the dropwise addition of water to decompose excess lithium aluminum hydride. Filter-aid (5 g) is thoroughly mixed with the precipitate and the mixture is filtered. The insoluble material is digested with three 2 mL portions of diethyl ether and the combined diethyl ether solutions are extracted with three 75 mL portions of 3N hydrochloric acid. After basification with sodium hydroxide, the aqueous portions are extracted with diethyl ether (four 100 mL portions) and the diethyl ether extracts are dried and evaporated to afford the title compound.

I claim:

1. A compound of Formula I $$\begin{array}{c} R^4-CH \\ | \\ R^3 \end{array} \quad R^2 \quad I$$

$$R \quad O \quad R^1$$

wherein R, $R^1$, and $R^2$ are each independently hydrogen, alkyl of from one to ten carbon atoms, alkynyl of from two to ten carbon atoms, phenyl or phenyl substituted by one to four substituents selected from the group consisting of alkyl, alkoxy, thioalkoxy, halogen, and trifluoromethyl; $R^3$ is hydrogen, hydroxy or alkoxy of from one to ten carbon atoms; and $R^4$ is selected from the group consisting of

[structures of heterocyclic rings]

a pharmaceutically acceptable acid addition salt thereof.

2. A compound according to claim 1, in which $R^4$ is

[structure]

3. A compound according to claim 2, in which $R^4$ is

[structure]

4. A compound according to claim 3 selected from the group consisting of:
α-(5-Ethyl-3-furanyl)-1-methyl-1H-imidazole-2-methanol;
α-(2-Ethyl-3-furanyl)-1-methyl-1H-imadazole-2methanol;

α-(4-Ethyl-3-furanyl)-1-methyl-1H-imidazole-2methanol;

α-(2-Ethyl-5-methyl-3-furanyl)-1methyl-1H-imidazole-b 2-methanol;

α-(4Ethyl-5-methyl-3-furanyl)-1methyl-1H-imidazole-2methanol.

5. A method of treating the symptoms of cognitive decline in an elderly patient comprising administering to a patient suffering therefrom a according to claim 1.

6. A pharmaceutical composition for the treatment of the symptoms of cognitive decline in an elderly patient comprising a cholinergically effective amount of a compound according to claim 1 in combination with a pharmaceutically acceptable carrier.

* * * * *

UNITED STATES PATENT AND TRADEMARK OFFICE
CERTIFICATE OF CORRECTION

PATENT NO. : 5,068,237
DATED : November 26, 1991
INVENTOR(S) : Sheila H. Hobbs

It is certified that error appears in the above-identified patent and that said Letters Patent is hereby corrected as shown below:

At Column 12, line 43, insert after "thereof" --, provided that when $R^3$ is hydrogen, $R^4$ is not

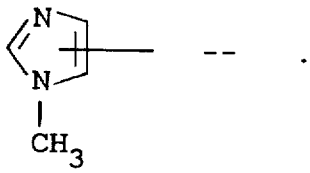 -- .

At Column 12, line 67, delete "2me-" and insert -- 2-me- --.

At Column 13, line 1, delete "2me-" and insert -- 2-me- --.

At Column 13, line 3, delete "1methyl" and insert -- 1-methyl --.

At Column 13, line 4, delete "b".

At Column 13, line 5, delete "4Ethyl" and insert -- 4-Ethyl -- and delete "1methyl" and insert -- 1-methyl --.

At Column 13, line 6, delete "2methanol" and insert -- 2-methanol --.

At Column 14, line 2, insert before "according" --compound--.

UNITED STATES PATENT AND TRADEMARK OFFICE
CERTIFICATE OF CORRECTION

PATENT NO. : 5,068,237

DATED : November 26, 1991

INVENTOR(S) : Sheila H. Hobbs

It is certified that error appears in the above-identified patent and that said Letters Patent is hereby corrected as shown below:

Column 14, line 2, after "therefrom a" insert --cholinergically effective amount of a --.

Signed and Sealed this

Thirteenth Day of April, 1993

Attest:

STEPHEN G. KUNIN

*Attesting Officer*       *Acting Commissioner of Patents and Trademarks*